United States Patent [19]

Kim et al.

[11] Patent Number: 5,770,770
[45] Date of Patent: Jun. 23, 1998

[54] REACTIVE DISTILLATION PROCESS AND EQUIPMENT FOR THE PRODUCTION OF ACETIC ACID AND METHANOL FROM METHYL ACETATE HYDROLYSIS

[75] Inventors: Ki-Joo Kim; Hang Duk Roh, both of Suwon-si, Rep. of Korea

[73] Assignee: Sunkyong Industries, Kyunggi-do, Rep. of Korea

[21] Appl. No.: 576,485

[22] Filed: Dec. 21, 1995

[30] Foreign Application Priority Data

Dec. 29, 1994 [KR] Rep. of Korea ...................... 94-38355

[51] Int. Cl.[6] ............................ C07C 51/42; C07C 53/08
[52] U.S. Cl. ............................................ 562/608; 203/88
[58] Field of Search ............................................. 562/608

[56] References Cited

U.S. PATENT DOCUMENTS 4,352,940 10/1982 Adelman et al. ....................... 562/608

*Primary Examiner*—Paul J. Killos
*Attorney, Agent, or Firm*—Oblon, Spivak, McClelland, Maier & Neustadt, P.C.

[57] ABSTRACT

The present invention is a reactive distillation process for methyl acetate hydrolysis comprising a rectifying section a reaction section and a stripping section. A water stream is fed into the upper portion of the rectifying or reaction zone and a methyl acetate stream is fed into the lower portion of the reaction zone which contains packings made of ion exchange resin. The products, acetic acid and methanol, are continuously produced from the bottom of the apparatus.

8 Claims, 2 Drawing Sheets

REACTIVE DISTILLATION PROCESS AND EQUIPMENT FOR THE PRODUCTION OF ACETIC ACID AND METHANOL FROM METHYL ACETATE HYDROLYSIS

BACKGROUND OF THE INVENTION

1. Field of the Invention

The present invention relates to the hydrolysis of methyl acetate to acetic acid and methanol by a reactive distillation process using ion exchange resins as catalysts. The present invention is especially useful for equilibrium-limited reactions such as hydrolysis and esterification, and separation of azeotropic mixtures.

2. Description of the Background

Methyl acetate (MA), one of the feed streams in this invention, is produced in great amounts as a byproduct from purified terephthalic acid (PTA) plants and polyvinyl alcohol (PVA) plants. Methyl acetate mixtures from PVA plants have an azeotropic composition of methyl acetate and methanol, and from PTA plants are a mixture of methyl acetate and water. In the present invention both mixtures and other mixtures containing methyl acetate more than 50% are referred to as methyl acetate mixtures.

Since methyl acetate is a less valuable solvent, methyl acetate is sold at a low price or hydrolyzed to methanol and acetic acid, which are more valuable solvents, by a hydrolysis reaction followed by conventional distillation processes. Conventional distillation after reaction, however, has some drawbacks. First of all, this complex process has low yield because the equilibrium constant which governs the hydrolysis reaction is small. The second drawback is high fixed costs and high operating costs resulting from separated hydrolysis reactors and four distillation towers including extractive distillation columns and two dehydration columns.

Further, the catalytic materials for hydrolysis or esterification reactions are, in general, liquid acid catalysts such as sulfuric acid and hydrochloric acid, which cause corrosion problems with equipment and separation problems between products and catalysts.

The first patent for reactive distillation of methyl acetate was U.S. Pat. No. 4,435,595. In contrast to the present invention, methyl acetate, the top product, was synthesized from methanol and acetic acid in that process and reactive distillation was conducted with a liquid catalyst, sulfuric acid.

An important objective of this invention is the design and optimization of operating conditions for hydrolysis of methyl acetate by a reactive distillation process.

SUMMARY OF THE INVENTION

The main purpose of the present invention was to design a reactive distillation method which eliminates many inherent problems such as low reaction yield, low product purity, corrosion problems, high fixed costs and operating costs caused by separated reaction and distillation processes.

Reactive distillation is a method to integrate reaction and distillation in the same column. Although reactive distillation has been known as one of unit operations since the 1920s, most of the reaction and distillation processes have been operated independently. The advantages of reactive distillation make it possible to develop commercial reactive distillation processes such as the production of MTBE (methyl-t-butyl ether), a clean octane enhancer, and synthesis of methyl acetate.

The advantages of the reactive distillation process for methyl acetate hydrolysis are more attractive than those of the conventional process, because integrating reaction and distillation technology in the same column reduces capital and operating costs greatly. Most hydrolysis or esterification reactions are limited by chemical equilibrium, but the reactive distillation process can shift the equilibrium reaction forward by removing the products, acetic acid and methanol, continuously from the reactants, methyl acetate and water. In cases where an azeotropic mixture is formed in the column, reactive distillation breaks azeotropic compositions resulting in an increase in reaction yield and selectivity.

Therefore, this invention provides a process to integrate the hydrolysis of methyl acetate and separation of products and reactants via a novel reactive distillation method.

More particularly, the invention provides a reactive distillation process for producing acetic acid and methanol as hydrolysis products from a byproduct composition containing more than 50% of methyl acetate, comprising the following steps:

(a) hydrolysing a mixture containing methyl acetate to acetic acid and methanol in a reaction zone, wherein ion exchange resin packing is present in the reaction zone as a catalyst, water is supplied downwardly to the ion exchange resin packing and the methyl acetate mixture is supplied upwardly to the ion exchange resin packing, (b) collecting unreacted methyl acetate and water vapor occupying the upper part of the reaction zone, condensing and resupplying them to the reaction zone, and (c) at the same time as step (b), collecting a reaction mixture from step (a) occupying the lower part of the reaction zone, separating the reaction mixture into the hydrolysis products and impurities by reboiling, re-supplying the impurities to the reaction zone and recovering the hydrolysis products.

In addition to the reactive distillation process, this invention provides a reactive distillation unit for methyl acetate hydrolysis, comprising a condenser wherein vapor flows are condensed to liquids, a reactive distillation column, and a reboiler.

The reactive distillation column of this invention has three novel zones which are a rectifying zone for further distillation, a reaction zone, and a stripping zone wherein products are separated from reaction mixtures.

In the present invention, the reactive distillation column has two feed locations, i.e., an upper location for water and a lower location for methyl acetate mixtures, respectively.

The reaction zone of this invention is packed with ion exchange resin, one of the least expensive solid catalysts. The solid catalyst eliminates corrosion and product separation problems at the same time. Ion exchange resins are used mainly in water treatment and can be classified into four types with respect to the type of functional groups. Strongly acidic ion exchange resins, one of the four types, are suitable for use in the invention as a catalytic material for hydrolysis and esterification reactions. The small bead size (0.4–1.1 mm) of conventional ion exchange resins may produce a high pressure drop, however, and small bead resin is preferably not used directly as a packing material in the invention. In the present invention, the ion exchange resin is preferably pelletized as a Raschig ring with the addition of an inert polymer as an adhesive.

Other features and advantages of the present invention will become more apparent from the following detailed description, taken in conjunction with the accompanying drawings which illustrate the principles of the invention. It should be understood, however, that the detailed description and specific examples, while indicating preferred embodiments of this invention, are given by way of illustration only, since various changes and modifications within the spirit and scope of the invention will become apparent to those skilled in the art from this detailed description.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
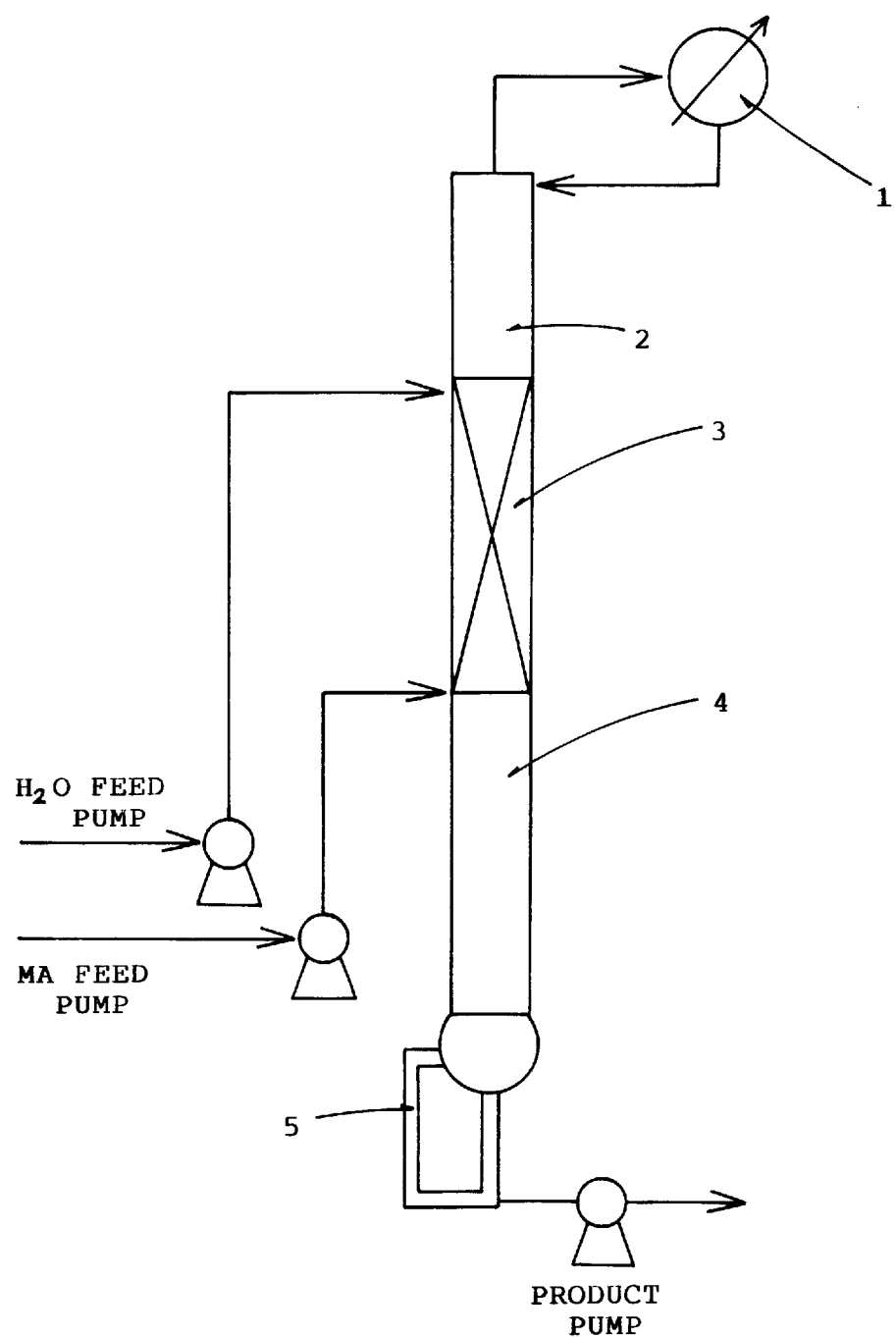
FIG. 1 is a schematic representation of a reactive distillation process with a rectifying zone where further separation proceeds.

As shown in the exemplary drawings, the reactive distillation unit has five major parts from the top of the column: a condenser (1), a rectifying zone (2), a reaction zone (3), a stripping zone (4), and a reboiler (5).

One of special characteristics of this invention is the double feed streams to the reactive distillation column. An upper feed pipe in the upper portion of the reaction zone supplies a water stream to the top of the reaction zone (3) or the rectifying zone (2). A lower feed pipe into the lower portion of the reaction zone supplies methyl acetate or a composition containing methyl acetate to the lower portion of the reaction zone. The hydrolysis reaction for upward moving methyl acetate and downflowing water is designed to run inside of and on the surface of the ion exchange resin packing. The molar ratio of water to methyl acetate is varied from 1 through 20. If the molar ratio is lower than 1, entrainment by too much methyl acetate vapor may flood the column. When the molar ratio is over 20, downflow flooding may occur due to heavy water flow.

Another characteristic feature of the present invention is the catalytic material for methyl acetate hydrolysis, which is a strongly acidic ion exchange resin. Any conventional strongly acidic ion exchange resin can be used in the present invention.

Suitable strongly acidic ion exchange resins are styrene and acrylic resins having sulfonic acid groups ($-SO_3H$) attached to an insoluble styrenic or acrylic polymer matrix. The bead size of a conventional resin is, however, generally so small that the resin and inert polymers are molded together into a conventional packing shape, such as a Raschig ring, Berl saddle, Intalox saddle or Pall ring, using conventional molding processes. The packing is then located or embedded in the reaction zone (3).

In general, 3–30% by weight of the inert polymers are added to the ion exchange resin. If the weight percent is lower than 3 percent, the inert polymers may not properly bond the ion exchange resin together. If the weight percent is higher than 30 percent, the active sites of the ion exchange resin are drastically reduced. As described above, the cationic exchange resin of the invention avoids corrosion and separation problems, but promotes gas-liquid mass transfer.

The number of theoretical plates is one of the most important factors in the distillation column. Considering reaction and distillation efficiency and column economics, the number of theoretical plates in the present invention is preferably 0–10 plates for the rectifying zone (2), 5–25 plates for the reaction zone (3) and 5–40 plates for the stripping zone (4). Zero theoretical plates in the rectifying zone (2) means no rectifying zone (2) in the column layout. Thus, the present invention includes a reactive distillation process without rectifying zone (2).

Reflux ratio is also an important factor in distillation tower design and operation. To increase reaction yield and selectivity, the condensed liquids are totally or substantially recycled to the column.

One of important operating factors in the invention is the temperature of the reboiler (5). The present invention has a range of temperature from 40° C. to 150° C. Insufficient separation of methyl acetate in the stripping zone (4) occurs at a temperature below 40° C. and entrainment flooding by methyl acetate vapor occurs at temperatures above 150° C.

The products, acetic acid and methanol, are separated in the stripping zone (4) and then obtained as products from the reboiler (5). The unreacted reactants, water and methyl acetate, move upward to the rectifying zone (2) and to the condenser (1) forming an azeotrope. All or a major portion of the condensed liquids are returned to the column to facilitate the hydrolysis reaction.

Figure 2:
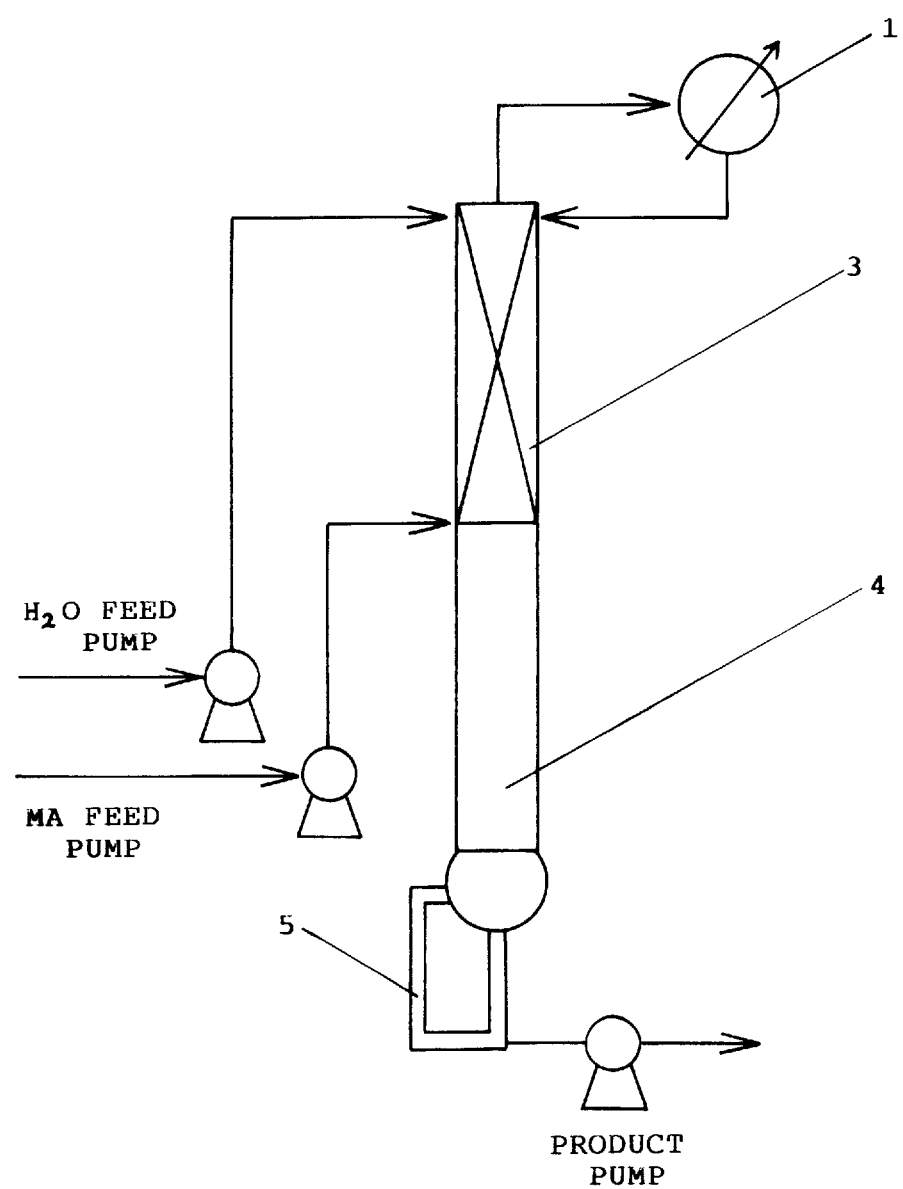
FIG. 2 is a schematic representation of a reactive distillation process without a rectifying zone. No further separation is required above the reaction zone.

In addition to the reactive distillation process with the rectifying zone (2), this process can be operated without the rectifying zone (2), as is shown in FIG. 2.

EXAMPLES

In the following examples, the catalytic material employed was Diaion PK 208H, manufactured by Mitsubishi Kasei, Japan and the inert polymer was purchased from Yukong Ltd., Korea.

Example 1

MA Feed=Pure methyl acetate

Reboiler Temperature=70.8° C.

Reaction zone temperature=57° C.

Reflux ratio=50

| FEED STREAM | |
|---|---|
| $H_2O$ Feed (ml/min) | 1.2 |
| MA Feed (ml/min) | 2.2 |
| Molar ratio | 2.5 |
| NO. OF THEORETICAL PLATES | |
| Rectifying zone | 2 |
| Reaction zone | 10 |
| Stripping zone | 30 |
| BOTTOM | |
| Reaction yield (%) | 99.2 |
| Methyl acetate (% by weight) | 0.81 |
| Acetic acid (% by weight) | 28.3 |

Example 2

MA Feed=Azeotropic mixture of methyl acetate with water
Reboiler Temperature=95.2° C.
Reaction zone temperature=57° C.
Reflux ratio=50

| FEED STREAM | |
|---|---|
| $H_2O$ Feed (ml/min) | 3.0 |
| MA Feed (ml/min) | 2.2 |
| Molar ratio | 6.0 |
| NO. OF THEORETICAL PLATES | |
| Rectifying zone | 2 |
| Reaction zone | 10 |
| Stripping zone | 20 |
| BOTTOM | |
| Reaction yield (%) | 99.5 |
| Methyl acetate (% by weight) | 0.47 |
| Acetic acid (% by weight) | 25.6 |

Example 3

MA Feed=Azeotropic mixture of methyl acetate with methanol
Reboiler Temperature=130.6° C.
Reaction zone temperature=57° C.
Reflux ratio=∞

| FEED STREAM | |
|---|---|
| $H_2O$ Feed (ml/min) | 7.4 |
| MA Feed (ml/min) | 2.2 |
| Molar ratio | 15.0 |
| NO. OF THEORETICAL PLATES | |
| Rectifying zone | 5 |
| Reaction zone | 15 |
| Stripping zone | 20 |
| BOTTOM | |
| Reaction yield (%) | 99.9 |
| Methyl acetate (% by weight) | 0.12 |
| Acetic acid (% by weight) | 20.1 |

Obviously, additional modifications and variations of the present invention are possible in light of the above teachings. It is, therefore, to be understood that within the scope of the appended claims, the invention may be practiced otherwise than as specifically described herein.

The priority document Korean Patent Application No. 94-38355 filed Dec. 29, 1994 is incorporated herein by reference in its entirety.

What is claimed as new and desired to be secured by Letters Patent of the United States is:

1. A reactive distillation process for producing acetic acid and methanol as hydrolysis products from a composition containing more than 50% of methyl acetate, comprising the steps of:

(a) hydrolysing said composition to acetic acid and methanol in a reaction zone having an upper portion and a lower portion, said reaction zone containing an acidic ion exchange resin catalyst, supplying water downwardly to said ion exchange resin catalyst and supplying said composition upwardly to said ion exchange resin catalyst to form a reaction mixture;

(b) collecting unreacted methyl acetate and water vapor in said upper portion of said reaction zone, condensing said collected methyl acetate and water vapor to form a condensate and resupplying said condensate to said reaction zone; and (c) at the same time as said step (b), collecting said reaction mixture from said lower portion of said reaction zone, separating said reaction mixture into acetic acid, methanol and impurities by reboiling, resupplying said impurities to said reaction zone and recovering said acetic acid and methanol.

2. The process of claim 1, wherein said composition is pure methyl acetate, a mixture of methyl acetate and water or a mixture of methyl acetate and methanol.

3. The process of claim 1, further comprising rectifying unreacted methyl acetate and water in said step (b) prior to said condensing.

4. The process of claim 1, further comprising rectifying unreacted methyl acetate and water prior to said resupplying to step (a).

5. The process of claim 3, further comprising rectifying unreacted methyl acetate and water prior to said resupplying to step (a).

6. The process of claim 1, wherein the temperature of said reaction zone is within a range of 40°–50° C.

7. The process of claim 1, wherein said composition and said water are supplied at a composition: water molar ratio within a range of 1:1–1:20.

8. The process of claim 1, where in step (b) the only materials collected in the upper portion of said reaction zone are unreacted methyl acetate and water vapor.

* * * * *